US010695158B2

(12) United States Patent
Johnsen et al.

(10) Patent No.: US 10,695,158 B2
(45) Date of Patent: Jun. 30, 2020

(54) IMPLANTABLE MEDICAL DEVICE WITH IMPROVED ORIENTATION

(71) Applicant: COOK MEDICAL TECHNOLOGIES LLC, Bloomington, IN (US)

(72) Inventors: Jeppe D. Johnsen, Froerup (DK); Bent Øhlenschlaeger, Ll. Skensved (DK); Christian Dela, Valby (DK); Torben Andersen, Taastrup (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 850 days.

(21) Appl. No.: 14/876,108

(22) Filed: Oct. 6, 2015

(65) Prior Publication Data

US 2016/0095688 A1    Apr. 7, 2016

(30) Foreign Application Priority Data

Oct. 7, 2014    (GB) .................................. 1417723.2

(51) Int. Cl.
*A61F 2/01*    (2006.01)
*A61B 17/12*    (2006.01)

(52) U.S. Cl.
CPC .......... *A61F 2/01* (2013.01); *A61B 17/12109* (2013.01); *A61B 17/12172* (2013.01); *A61F 2002/016* (2013.01); *A61F 2220/0058* (2013.01); *A61F 2230/005* (2013.01); *A61F 2230/0067* (2013.01); *A61F 2240/001* (2013.01); *A61F 2250/0006* (2013.01)

(58) Field of Classification Search
CPC ...... A61F 2/01; A61F 2/013; A61F 2002/016; A61F 2002/018
See application file for complete search history.

(56) References Cited

U.S. PATENT DOCUMENTS

| 4,425,908 | A |   | 1/1984 | Simon |
|---|---|---|---|---|
| 4,832,055 | A |   | 5/1989 | Palestrant |
| 5,836,969 | A | * | 11/1998 | Kim ......................... A61F 2/01 606/200 |
| 6,231,589 | B1 |   | 5/2001 | Wessman et al. |
| 7,896,898 | B2 |   | 3/2011 | WasDyke |
| 8,062,326 | B2 |   | 11/2011 | McGuckin, Jr. et al. |
| 8,500,774 | B2 |   | 8/2013 | McGuckin, Jr. et al. |

(Continued)

OTHER PUBLICATIONS

Combined Search and Examination Report for GB 1417723.2, dated Mar. 24, 2015.

*Primary Examiner* — Christopher L Templeton
(74) *Attorney, Agent, or Firm* — Brinks Gilson & Lione

(57) ABSTRACT

An implantable medical device such as a filter has a generally conical shape formed by a set of filter legs extending from a free distal end to an apex of the assembly and specifically to a coupling device. A retrieval element such as a hook extends from the hub of. A spacer member is disposed at the hub and is formed of a plurality of curved wire elements. The spacer member has a radius or width smaller than the greatest radius of the filter device, defined by the free ends of the filter legs. The spacer member allows the filter assembly to tilt within a vessel but limits the tilt to a maximum desired or permitted tilt, ensuring that the retrieval device remains spaced from the vessel wall and therefore not subject to tissue ingrowth.

21 Claims, 5 Drawing Sheets

(56) References Cited

U.S. PATENT DOCUMENTS

| | | | |
|---|---|---|---|
| 2004/0215230 A1* | 10/2004 | Frazier | A61B 17/12022 606/200 |
| 2005/0038470 A1* | 2/2005 | van der Burg | A61B 17/0057 606/213 |
| 2005/0107822 A1* | 5/2005 | WasDyke | A61F 2/01 606/200 |
| 2005/0288704 A1* | 12/2005 | Cartier | A61F 2/01 606/200 |
| 2006/0079928 A1* | 4/2006 | Cartier | A61F 2/01 606/200 |
| 2006/0203769 A1 | 9/2006 | Saholt et al. | |
| 2007/0173885 A1 | 7/2007 | Cartier et al. | |
| 2007/0198050 A1* | 8/2007 | Ravenscroft | A61F 2/01 606/200 |
| 2007/0213685 A1* | 9/2007 | Bressler | A61F 2/01 604/500 |
| 2008/0221609 A1* | 9/2008 | McGuckin | A61F 2/01 606/200 |
| 2008/0294188 A1* | 11/2008 | Appling | A61F 2/0095 606/200 |
| 2009/0005803 A1* | 1/2009 | Batiste | A61F 2/01 606/200 |
| 2009/0198270 A1 | 8/2009 | McGuckin, Jr. et al. | |
| 2010/0049238 A1 | 2/2010 | Simpson | |
| 2010/0049239 A1* | 2/2010 | McGuckin, Jr. | A61F 2/01 606/200 |
| 2013/0274793 A1* | 10/2013 | McGuckin, Jr. | A61F 2/01 606/200 |
| 2014/0074146 A1* | 3/2014 | Fischer, Jr. | A61F 2/01 606/200 |
| 2015/0005809 A1* | 1/2015 | Ayres | A61F 2/01 606/200 |
| 2015/0012034 A1* | 1/2015 | McGuckin, Jr. | A61F 2/01 606/200 |
| 2017/0181751 A1* | 6/2017 | Larsen | A61B 17/0057 |

* cited by examiner $$x = \sqrt{45^2 + 17^2} = 48.01$$
$$\tan 15° = \frac{a}{b} \Rightarrow b \cdot \tan 15° = a$$
$$a = 45 \cdot \tan 15° = 12.05 \text{ mm}$$
$$r_{min} = (17-a)\text{mm} = 17-12.05 = 4.95 \text{ mm}$$

IMPLANTABLE MEDICAL DEVICE WITH IMPROVED ORIENTATION

CROSS-REFERENCE TO RELATED APPLICATIONS

This application claims the benefit of priority under 35 U.S.C. § 119(a) to Great Britain Patent Application No. GB 1417723.2, filed Oct. 7, 2014, which is hereby incorporated by reference in its entirety.

TECHNICAL FIELD

The present invention relates to an implantable medical device such as a vascular filter or occluder.

BACKGROUND ART

Vascular filters are well known in the art. They are generally used for filtering blood in a patient's vessels, such as but not exclusively the inferior vena cava (IVC). Such filters may be implanted substantially permanently, for example for treating deep vein thrombosis, or may be temporarily left in a patient for instance during surgery or during the course of a temporary ailment.

A common and advantageous design of filter has a conical shape, formed of a plurality of filter legs expanding outwardly from a central hub. The filter, which can conveniently be deployed by endoluminal administration typically through the jugular or femoral vein, is oriented with its narrowing taper along the direction of blood flow such that the wide end of the filter is upstream of the hub. Blood clots and other debris are caught by the filter legs, where blood clots may dissolve by natural clot lysing. The conical form of the filter is naturally biased into the open configuration, not only by inherent resiliency of the filter structure but also by blood pressure. The filter can be retrieved by withdrawing the filter back into a retrieval catheter. For this purpose it is known to have a retrieval device, such as a hook, at the hub end of the filter.

A problem can occur with such filters when in situ in that they can tilt relative to the vessel to an extent which results in loss of good coupling of the filter to the vessel wall, leading to leakage of unfiltered blood around the filter and, importantly, to any retrieval element such as a hook contacting the vessel wall and becoming embedded in the vessel wall as a result of endothelialisation. When this occurs it becomes difficult if not impossible to remove the filter by an endoluminal procedure, resulting in the need for open surgery.

Regulatory authorities, such as the United States Food and Drug Administration (FDA) prescribe required performance parameters such as a maximum permissible tilt angle and maximum amount of tenting of implantable vascular filters and the like. It is known for such purposes to have filter stabilisation devices incorporated in the filter assembly for keeping the filter precisely aligned in the vessel, that is with the hub positioned centrally in the vessel. Some designs of stabilisation devices can become embedded in the vessel wall by endothelialisation and hence become difficult to remove, while other designs involve the use of long lengths of wire or thread which can become entangled with the legs of the filter, leading to improper deployment of the filter.

Some examples of implantable vascular filters are disclosed in U.S. Pat. No. 8,062,326, US 2006/0203769, U.S. Pat. No. 6,231,589, US 2010/0049238, U.S. Pat. Nos. 4,832,055, 7,896,898 and 4,425,908.

DISCLOSURE OF THE INVENTION

The present invention seeks to provide an improved implantable medical device such as a vascular filter, for instance a filter for the inferior vena cava. The teachings herein extend to other medical devices including but not limited to occlusion devices.

According to an aspect of the present invention, there is provided an implantable medical device including: coupling member; a plurality of leg elements made of flexible material, each leg element including a first end connected to the coupling member and a second end remote from the connecting member, the leg elements extending in a deployed conical configuration from the coupling member to a maximum radius of the leg elements adjacent the second end of the leg elements, the maximum radius providing a maximum diameter to the medical device; and a spacer member disposed proximate the coupling member; the spacer member having a deployed radius less than the maximum radius of the leg elements.

The structure of device specified above does not prevent tilt of the device when implanted in a vessel, and in practice can allow the filter to tilt from the vessel centreline. In practice, the spacer member has a radius which is substantially less than the radius of the vessel to which the medical device is sized, such that in use if one side of the spacer member contacts the vessel wall, the opposing side of the spacer member will be spaced from the vessel wall.

The spacer member ensures that the coupling member does not contact the vessel wall and hence that the coupling member does not become embedded in the vessel wall as a result of endothelialisation. Furthermore, the relatively smaller size of the spacer member reduces the amount of material needed for the spacer member as well as reducing the risk of entanglement with the filter legs. Moreover, in practice only a part of the spacer member may contact the vessel wall, leading only to partial endothelialisation of the spacer member as opposed to complete endothelialisation as occurs with prior art devices.

Advantageously, the spacer member has a deployed radius substantially the same as a minimum distance between the position of the coupling member to the maximum diameter of the medical device when at a maximum allowed angle of tilt. In other words, the spacer member can allow the medical device to tilt up to the maximum allowable angle of tilt. The maximum allowable angle of tilt is normally determined by the regulatory authorities such as the US Food and Drug Administration (FDA), as well as by the filter geometry.

Preferably, the spacer member has a radius determined by the following equation:

$$R_{min} = (\text{rad}_d - b \tan x°),$$

where: $R_{min}$=minimum desired radius of the spacer member, $\text{rad}_d$=deployed maximum radius of the medical device, b=the length of the leg elements measured in a longitudinal direction of the device from the second ends to the coupling member, and x°=the maximum permitted tilt angle of the filter.

In a preferred embodiment the spacer member has a deployed radius of no more than 1.5 times $R_{min}$. The spacer member may have a deployed diameter of no more than 50% of the maximum diameter of the medical device.

The spacer member is advantageously formed of at least one curved wire element, preferably of two or more curved wire elements.

The wire element or elements extend in an embodiment around a part of the circumference of the spacer member.

In a practical embodiment, the spacer member is formed of two or more curved wire elements disposed substantially radially opposite one another and which are circumferentially spaced from one another.

Preferably, the or each wire element includes a curved vessel contact portion and a free end having a radius no greater than a radius of curvature of the vessel contact portion.

Advantageously, the or each wire element includes a reverse curved portion relative to the curvature of the vessel contact portion. The or each reverse curved portion may be adjacent the coupling member.

This structure of wire element confers a resiliency to the spacer member, useful in holding the coupling element spaced from the vessel wall, particularly during natural movement of the vessel wall.

The or each wire element is preferably attached at a single end thereof to the coupling member, the second end thereof being free. This enables the wire elements to be removed readily with the device even when there has been endothelialisation around the spacer member or, in practice a part of the device.

Preferably, the spacer member is substantially planar and lies in a plane substantially perpendicular to a longitudinal axis of the device. In an embodiment, the spacer member may lie at an angle of no more than ±25°, more preferably of no more than ±20° from a plane perpendicular to the longitudinal axis.

The medical device may be a filter, such as a vena cava filter, an occlusion device or other medical device.

According to another aspect of the present invention, there is provided a method of manufacture of an implantable medical device, the medical device including a coupling member; a plurality of leg elements made of flexible material, each leg element including a first end connected to the coupling member and a second end remote from the connecting member, the leg elements extending in a deployed conical configuration from the coupling member to a maximum radius of the leg elements adjacent the second end of the leg elements, the maximum radius providing a maximum diameter to the medical device; the method including the steps of: forming a spacer member and disposing the spacer member proximate the coupling member, wherein the step of forming the spacer member includes sizing the spacer member to have a deployed radius less than the maximum radius of the device.

Advantageously, the step of forming the spacer member includes sizing the spacer member to have a deployed radius substantially the same as a minimum distance between the position of the coupling member to the maximum deployed diameter of the medical device when at a maximum allowed angle of tilt.

Preferably, the step of forming the spacer member includes sizing the spacer member to have a deployed radius determined by the following equation:

$$R_{min}=(rad_d - b \tan x°),$$

where: $R_{min}$=minimum desired radius of the spacer member, $rad_d$=deployed maximum radius of the medical device, b=the length of the leg elements measured in a longitudinal direction of the device from the second ends to the coupling member, and x°=the maximum tilt angle of the filter.

Other features and advantages will become apparent from the description which follows and in the accompanying drawings.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
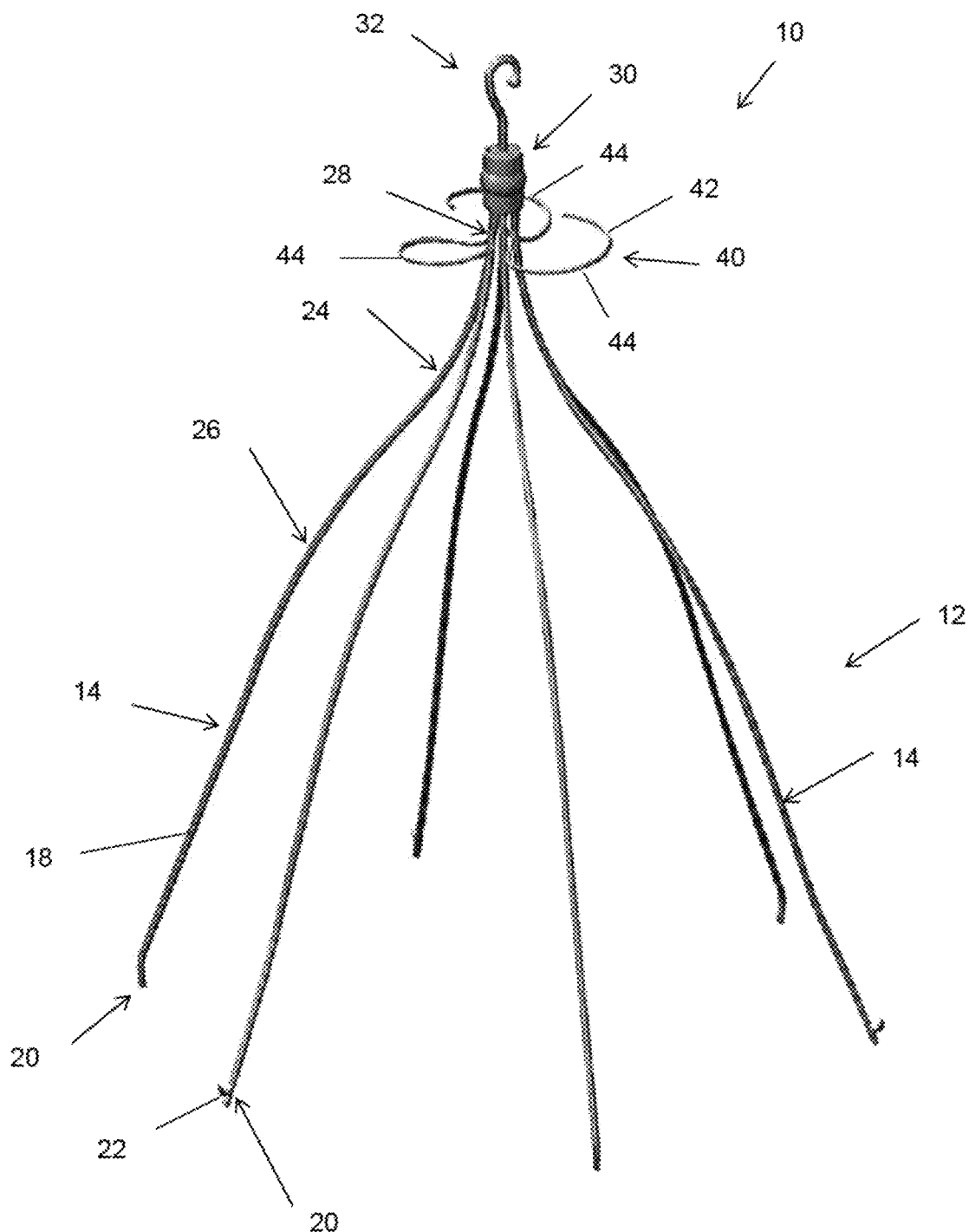
FIG. 1 is a perspective view from above of an embodiment of vascular filter device.

The accompanying drawings are schematic only. It is to be understood that the dimensions and proportions of the various components of the devices shown in the drawings are not to scale or in proportion relative to one another. It is also to be understood that the drawings depict only the principal components of the devices shown therein and that other elements normally found in such devices which are not central to understanding the teachings herein have been omitted for the sake of clarity.

The preferred embodiments described below are designed as vascular filters, particularly suitable for the inferior vena cava. It is to be understood, though, that these are examples only and that the teachings herein can be applied to other vascular filters as well as to other implantable medical devices including but not limited to vascular occluders. An occluder could be constructed from the devices shown in the drawings by fitting an occluding membrane to the legs so as to provide an occluding barrier across the surface of the device.

Referring first to FIG. 1, this shows an embodiment of vascular filter 10 suitable for deployment in the inferior vena cava. The filter assembly 10 includes a generally conical portion 12 formed of a plurality of first filter legs 14. In the example shown, each filter leg 14 includes a generally straight portion 18 having a free end 20 which may terminate with an outwardly extending barb 22 for fixation to a vessel wall. As barbs are well known in the art, the structure of the barb 22 is not described further herein as it may take a form of any known or otherwise suitable an anchoring barb. Not all of the filter legs 14 need be provided with anchoring barbs 22 and as can be seen, the embodiment of FIG. 1 has a barb 22 on every other one of the leg elements 12.

Each leg 14, in this example, also includes outwardly and inwardly curved portions 24 and 26 respectively, which have curvatures such as to cause the filter legs 12 to adopt a conical arrangement as shown in FIG. 1.

Each leg element 14 has a second leg end 28 which is attached to or integral with a coupling member 30, which may be a tubular element with a recess or bore disposed therein for receiving the second leg ends 28. The leg ends 28 may be fixed to the coupling member 30, for instance by welding, bonding, by a friction fit or the like. In another embodiment, the leg ends 28 may be formed as a part of the coupling member 30, for example their being laser cut from a common intermediate element.

Attached to the coupling member 30 is a retrieval device 32, which in this example is a hook. Retrieval devices of this nature are well known in the art.

The shape of the leg elements 14 of the filter assembly 10 shown in FIG. 1 is such that the device has its greatest deployed radius or, collectively, diameter at the free ends 20 of the legs 12 and a narrowest radius or diameter at the coupling member 30.

The legs 30 may be formed of wires although could in other embodiments be laser cut from a common cannula or rod, as is known in the art. The legs may be made of a spring material, such as spring steel, or shape memory alloy such as nickel titanium alloy, particularly Nitinol. The legs 14, will, therefore, naturally tend to open to the shape shown in FIG. 1 and in practice to press the free ends 20 of the legs 12 against the internal wall surface of a vessel.

Located adjacent the coupling member 30 and in a preferred embodiment attached thereto is a spacer member 40. The spacer member is, in the embodiment shown in FIG. 1, formed of three curved wire elements 42 which are spaced circumferentially with respect to one another around the coupling member 30. The spacer member 40 has an outer perimeter formed by the curved wire elements 42, which has a maximum radius substantially less than the expanded radius of the filter legs 12 at their point of maximum radius, that is at their free ends 20 in this embodiment.

As will be apparent in FIG. 1, the outer periphery of the spacer member 40 is provided by the curved surfaces of the wire elements 42 and in particular those portions 44 of the curved surfaces which are radially most distant from the coupling member 30. The shape of the curved wire elements 42 is described in further detail below in connection with FIG. 3.

In FIG. 1, the spacer member 40 is disposed in what could be described at a position below the coupling member 30, specifically to the side of coupling member 30 adjacent to the leg elements 14 and remote from the retrieval device 32. As will be apparent from FIG. 2, the spacer member 40 could be located elsewhere than in the precise position shown in FIG. 1.

The spacer member 40, particularly the curved wire elements of the embodiment shown in FIG. 1, could be formed from a variety of materials, including the same materials as the filter legs 12. In the preferred embodiment, the wire elements 42 are formed of a copper chromium nickel alloy such as Elgiloy. In other embodiments they could be made of a shape memory alloy such as Nitinol or a metal such as spring steel, or other suitable metal or alloy.

It should be apparent from the above description and FIG. 1 that the filter 10 has a shape which is generally circular when viewed in top or bottom plan and the coupling member 30 is likewise circular, thereby mimicking the general shape of a vessel, useful in ensuring full and precise coupling to the vessel wall when the filter assembly 10 is deployed.

Figure 2:
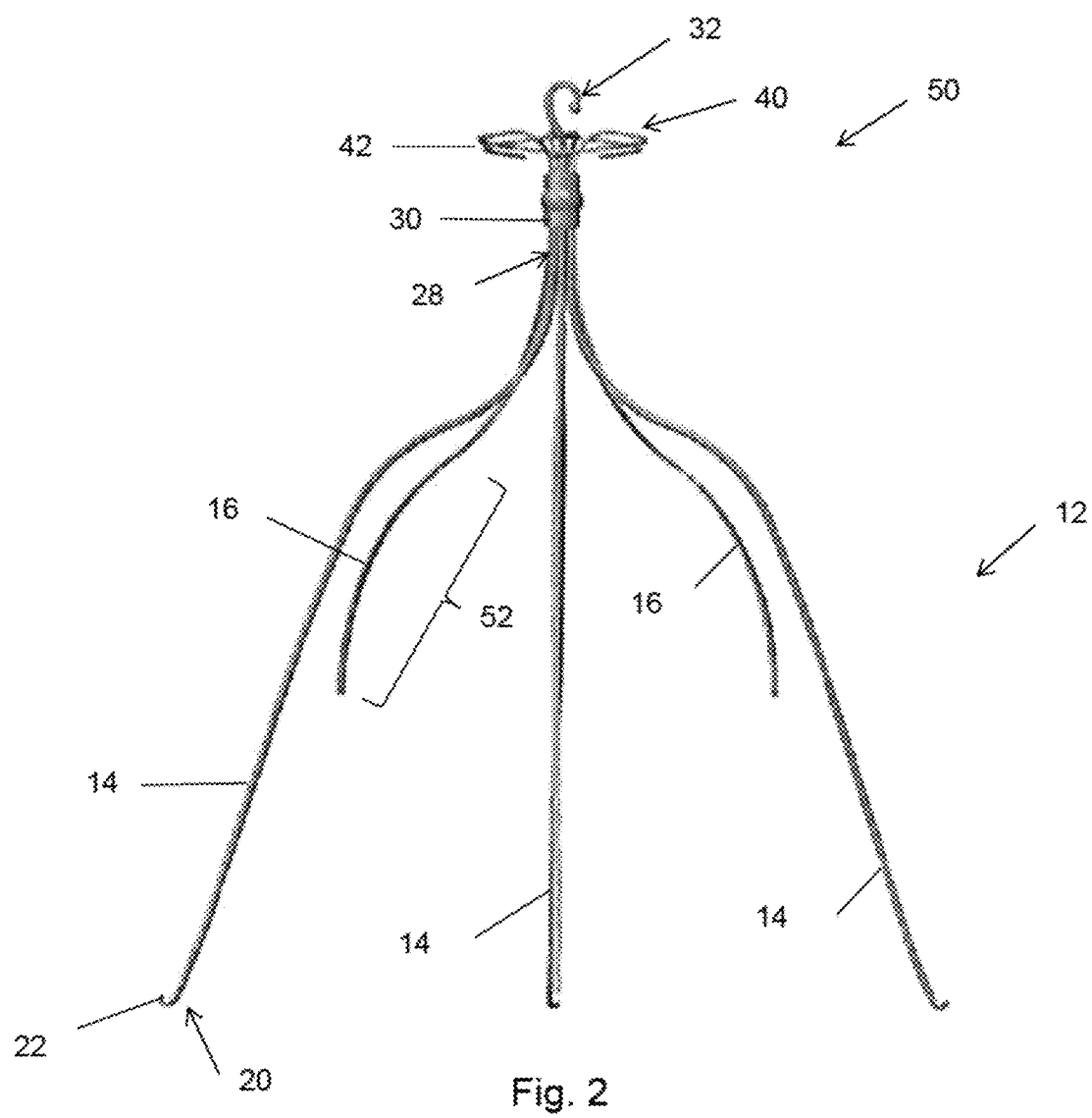
FIG. 2 shows a side elevational view of another embodiment of vascular filter device.

Referring now to FIG. 2, this shows another embodiment of implantable filter device 50 which is very similar to the filter assembly 10 of the embodiment of FIG. 1. The device 50 includes a set of first legs 14 similar to those of the embodiment of FIG. 1, a coupling member 30 and a retrieval device 32, again which are the same as those of the embodiment of FIG. 1. The embodiment of FIG. 2 also includes a plurality of second filter legs 16, which in this example are shorter in length than the plurality of first filter legs 14. Furthermore, the plurality of second filter legs 16 have a portion 52 which has a substantially continuous inward curvature as depicted in FIG. 2. In practice, the second filter legs 16 are located in the spaces between adjacent filter legs 14 in an interdigitated manner, thereby reducing the size of the gaps through the filter assembly 50 in order to trap debris of smaller size compared to the example in FIG. 1.

In practice, the plurality of first legs 14 will be partially radially compressed when disposed in a vessel, such that the plurality of second legs 16 will abut against the vessel wall.

In the embodiment of FIG. 2, the spacer member 40, which has a structure of curved wire elements 42 similar to the embodiment of FIG. 1, is disposed on the other side of the coupling member 30 and in particular on the side adjacent the retrieval device 32. This will be apparent from the view of FIG. 2. As will be apparent also from FIG. 2, the curved wire elements 42 of the spacer member 40 extend from the coupling member 40 and are advantageously attached thereto or integral therewith, in a manner similar to the legs 14 and 16 of the filter assembly 50. The curved wire elements 42 may have ends adjacent the coupling member 30 which are curved generally in the longitudinal direction of the filter device 50, for fitting into the coupling member 30, and intermediate portions which extend radially outwardly as shown in FIG. 2, to the curved portions 42.

Figure 3:
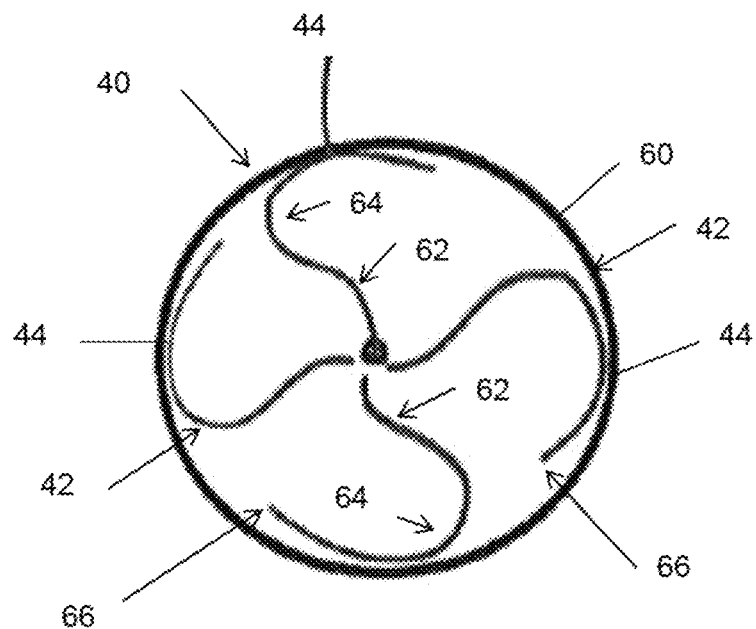
FIG. 3 is a plan view of a spacer member of the embodiments of FIGS. 1 and 2, depicted deployed in a vessel.

Referring now to FIG. 3, this shows the spacer member 40 in plan view. The circular boundary 60 is not an element of the filter assembly but intended to depict in general terms the periphery of the spacer member 40. The curved wire elements 42 extend from the central hub or coupling member 30. In the example shown in FIG. 3 there are provided four curved wire elements 32 substantially equally radially spaced around the coupling member 30, each curved wire element 42 having a first portion 62 adjacent the hub 30 which curves in a first direction and a second portion 64 beyond the first portion 62 which curves in the opposite direction, continuing to curve towards a free end 66 of the wire element 42. The second curved portion 64 may have a generally even radius of curvature throughout its length or may have a slightly flattened shape, that is with a greater radius of curvature in the zone adjacent in the peripheral boundary 60, and in particular to have a radius which approximates the radius of the circular peripheral boundary 60.

As will be seen in FIG. 3, the curved wire elements 42 have free ends 66 of relatively shallow curvature, extending almost straight. In particular, the ends 66 preferably do not curve back on themselves.

The double curvature formed by the portions 62, 64 of the curved wire elements 42 can in enhance the springiness of the elements 42 in the radial direction of the spacer member 40, useful in adjusting to any natural movement of the vessel wall.

Figure 4:
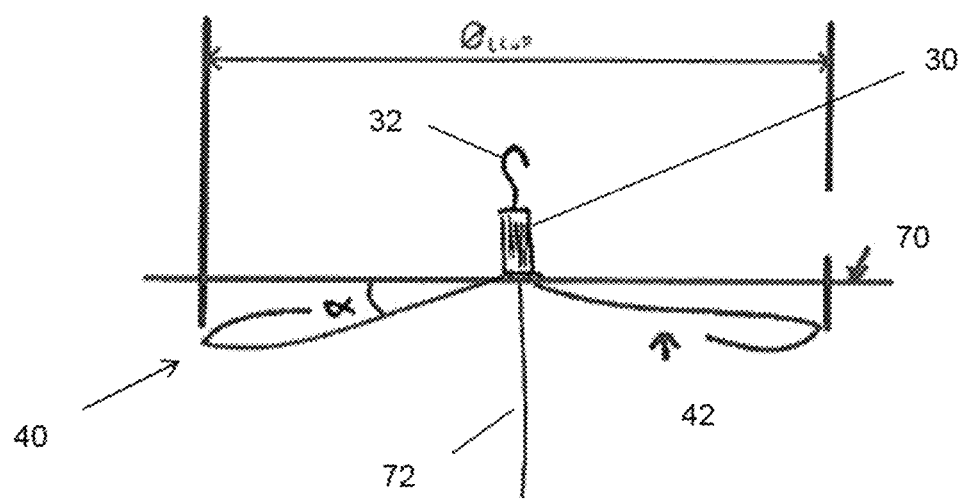
FIG. 4 is a side elevational view of another embodiment of vascular filter.

Referring now to FIG. 4, this shows a schematic diagram of the spacer member 40 in enlarged form and represented against a reference line 70 which is indicative of a plane normal, or perpendicular, to the longitudinal axis 72 of the filter assembly 10, 50. As will be apparent from FIG. 4, the curved wire elements 42 of the spacer member 40 are preferably disposed at an angle α to the perpendicular lines 70, the angle preferably being in the range of ±25° more preferably of ±20°. It will be appreciated, though, that in other embodiments the wires could lie in the plane 70 normal to the longitudinal axis 72 of the filter assembly 10, 50, as well as above the plane 70, that is in a direction towards to the retrieval element 32 and in practice away from the first filter legs 14.

Figure 5:
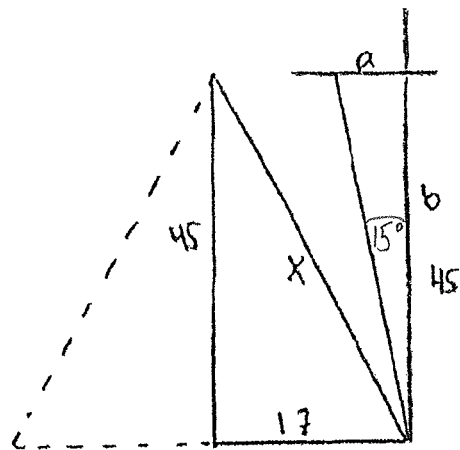
FIG. 5 shows an example of method of determining the diameter or radius of a spacer member for the implantable medical device taught herein.

Referring to FIG. 5, this shows an example of the geometry of a filter assembly in relation to a desired maximum tilt angle and how the radius of the spacer member can be determined. In the example of FIG. 5, the example filter assembly has an axial length (from the distal end to the proximal end of the assembly) of 45 mm nominally, with a maximum radius at the ends of the filter legs 14 of 17 mm before deployment, thereby giving, as shown, a length of filter legs in the region of 48 mm. The apex of the triangle shown in FIG. 5 represents the coupling member or hub 30.

Assuming a maximum permitted or desired angle of tilt of 15°, the displacement of the narrower end of hub 30 of the filter assembly from the centre line, that is parameter a in FIG. 5, can be determined by the following equations:

$$x = \sqrt{45^2 + 17^2} = 48.01$$
$$\tan 15° = \frac{a}{b} \Rightarrow b \times \tan 15° = a$$
$$a = 45 \times \tan 15° = 12.05 \text{ mm}$$

Having determined the dimension a, it is then possible to determine the minimum desired radius of the spacer member 40, namely:

$$r_{min} = (17-\alpha) \text{ mm} = 17 - 12.05 = 4.95 \text{ mm}$$

Thus, by having a spacer member with a radius, in this example, of at least 4.95 mm, not only will the spacer member 40 ensure that the filter cannot tilt beyond the maximum desired tilt, but this will also ensure that the retrieval device 32 will not come into contact with the vessel wall and therefore will not become embedded within the vessel wall through endothelialisation. It will be appreciated that the spacer member 40 could have a radius greater than the minimum and in some embodiments could have a radius of around 1.5 times the minimum diameter, or of 50% of the maximum deployed diameter of the medical device.

In practice, the spacer member 40 of the preferred embodiment has a deployed radius substantially the same as a minimum distance between the position of the coupling member to the maximum deployed radius of the medical device when at a maximum allowed angle of tilt. Thus, the spacer member can allow the medical device to tilt up to the maximum allowable angle of tilt. The maximum permitted angle of tilt is normally determined by the regulatory authorities such as the US Food and Drug Administration (FDA), as well as by the filter geometry.

The skilled person will appreciate that the actual dimensions and proportions of a particular device will be dependent upon the relative dimensions of the device, the dimensions of the vessel in which the device is to be positioned and the desired or permitted maximum angle of tilt. Where a greater angle of tilt may be permitted or desired, the diameter of the spacer member may be reduced and as a result also the length of the wire elements 42 of the spacer member. In contrast, where a smaller angle of tilt is permitted or desired, the spacer member will have a greater diameter.

Figure 6:
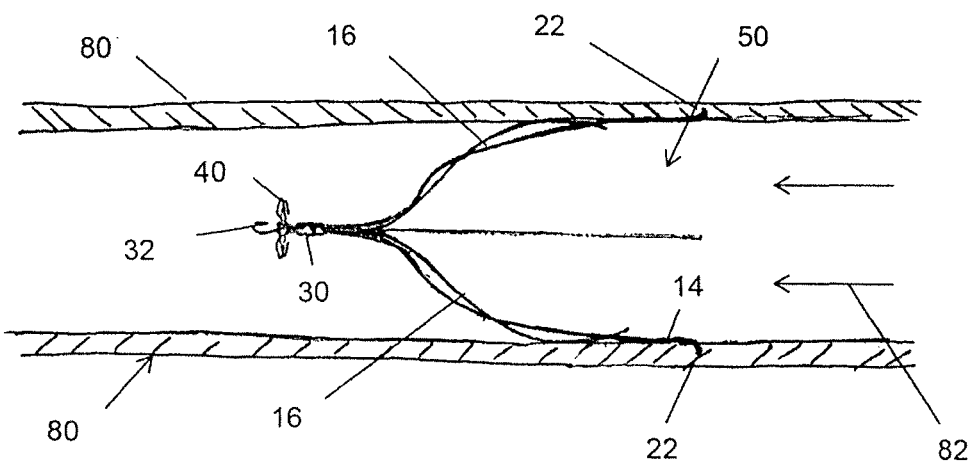
FIG. 6 is a perspective view from above of the embodiment of vascular filter of FIG. 2 deployed in a patient's vessel.
Figure 7:
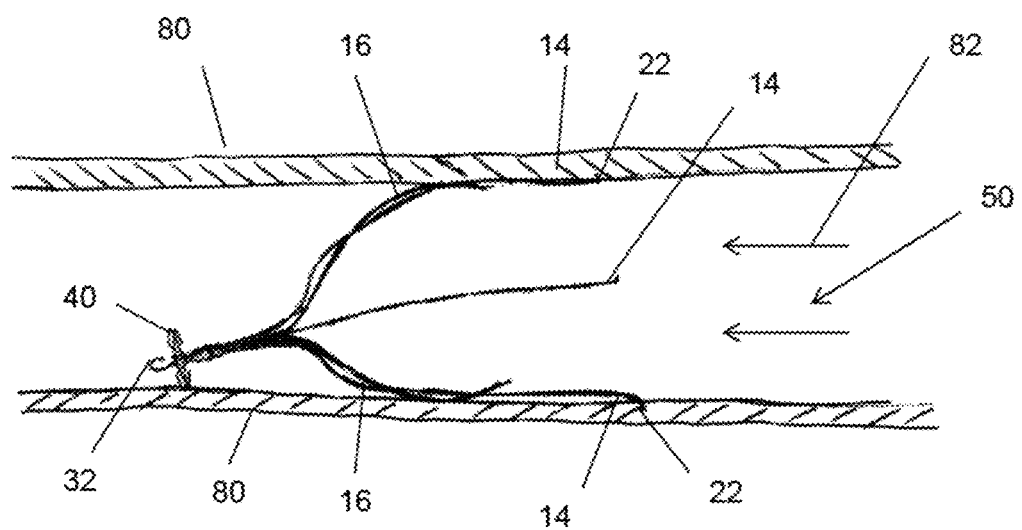
FIG. 7 is a view of the vascular filter of FIG. 6 tilted in the vessel.

Referring now to FIGS. 6 and 7, these show the embodiment of device of FIG. 2, implanted in a patient's vessel 80. As can be seen in FIG. 6, the implantable medical device 50 resides within the vessel, with the barbs 22 of the leg elements 14 embedded within the wall of the vessel 80 and with the set of second legs 16 pressing against the vessel wall at a position spaced from the barbs, thereby to provide two vessel contact points to the device. In the view of FIG. 6, the filter 50 is aligned with the vessel wall, such that the longitudinal axis of the device 50 is substantially parallel to the longitudinal axis of the vessel 80. In this configuration, the hub 30 end of the device and the retrieval element 32 are disposed generally in the centre of the vessel 80, this being the optimum configuration for the filter 50. As the skilled person will appreciate, unless held in this position such filters will rarely sit precisely aligned with the axis of the vessel and will more often than not tilt, in a manner depicted in FIG. 7. As can be seen in FIG. 7, the filter assembly 50 is shown tilted to the maximum amount possible given the design of the filter assembly 50. The set of first legs 14 remain in contact with the vessel wall, as do the legs 16 of the second plurality of legs. Even when tilted, the spacer member 40 not only prevents further tilt of the filter assembly 50 within the vessel 80 but also ensures that the retrieval device 32 at the proximal, narrow, end of the filter assembly 50 remains spaced from the vessel wall 80. As a result, any growth of vessel tissue around the retrieval element 32 is avoided. The retrieval element 32 thus remains exposed for attachment to a retrieval device (not shown) for removing the filter assembly 50 from within the patient's vessels after the end of the medical procedure. For this purpose, it is useful for the curved wire elements 42 of the spacer member to be made of wires attached only at one end. This enables the wires to be slid out from any ingrown tissue generated through endothelialisation as a result of having their remote ends unattached or free from attachment. Thus, the entire device 50 can be removed readily from within the patient's vasculature.

Moreover, as will be apparent in particular from FIGS. 1 and 2, the wire elements 42 forming of the spacer member 40 are relatively shorter and substantially shorter than the wires forming the legs 14 and, where provided, the set of second legs 16. As a result of the short length of the wires 32, there is substantially less chance of the wires becoming entangled with the legs 12 and/or the second legs 14 where provided. Entanglement can occur with structures having stabilising or spacing devices which are substantially larger in diameter. The use of shorter length of wire also reduces the amount of foreign material in the patient's body.

The filter legs and the wires forming the spacer element could be formed of any conventional material, examples including nickel titanium alloy (such as Nitinol), cobalt chromium nickel alloy (such as Elgiloy), stainless steel and the like. The filter legs and wires of the spacer member 40 can be made from the same or different materials.

As will be appreciated, the structure disclosed herein does not prevent the tilting of a filter but produces or eliminates the negative effects of over tilting.

The filter can have solely one set of first filter legs while other embodiments can have a combination of primary and secondary filter legs for optimising radial force and filtration function.

The wire elements of the spacer member can be described as anti-growth loops, being designed as open loops that is being connected at one end only to the other components of the filter assembly, in a preferred embodiment to the coupling member or hub 30. Advantageously, as shown in FIGS. 1 and 2, and in particular, the connection of the spacer member is preferably as close as possible to the apex of the structure of the filter.

The wires 42 of the spacer member 40 although preferably curving all in the same directions may curve in opposite directions relative to one another.

It will be appreciated also that the wire elements of the spacer member can contribute to filter efficiency, by acting as debris catching elements also. In such an event, the filter legs can be made of thinner material and/or be fewer in number.

Although the spacer member of the preferred embodiments has a generally round perimeter, other embodiments may have spacer members with different perimeters, for instance oval or polygonal. In this regard, the term radius used herein is intended to be representative of the lateral dimension of the spacer member.

It is to be understood that the teachings herein are not limited to a particular structure of filter and could be used in any other conical or tiltable implantable medical device. By way of example only, the teachings herein could be applied to a Cook Celect™ filter, a Günther Tulip™ vena cava filter and other similar filters. Equally, the teachings herein could be used for other types of implantable medical device, including occluders.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. An implantable medical device for a vessel, the implantable medical device including:
a coupling member defining a longitudinal axis;
a plurality of leg elements made of flexible material, each leg element including a first end connected to the coupling member and a second end remote from the connecting member, the leg elements extending in a deployed conical configuration from the coupling member to a maximum radius of the leg elements adjacent the second end of the leg elements, the second end of the leg elements defining a maximum diameter to the medical device; and
a spacer member disposed proximate the coupling member; the spacer member having a deployed radius less than the maximum radius of the leg elements, the spacer member being formed of a plurality of wire elements,
wherein each of the wire elements includes a first portion and a second portion, and wherein, when viewed along the longitudinal axis from the second end,
the first portion arcuately extends outward from the coupling member in a counterclockwise direction for a first length of the wire element and the second portion arcuately and continuously extends from the first portion in a clockwise direction for a second length of the wire element, which is greater than the first length, to a free end of the wire element, and the free end of each wire element is shaped to extend radially inward from a vessel contact portion of the wire element, or
the first portion arcuately extends outward from the coupling member in the clockwise direction for a first length of the wire element and the second portion arcuately and continuously extends from the first portion in the counterclockwise direction for a second length of the wire element, which is greater than the first length, to a free end of the wire element, and the free end of each wire element is shaped to extend radially inward from a vessel contact portion of the wire element.

2. The implantable medical device according to claim 1, wherein the spacer member allows tilting of the medical device in use.

3. The implantable medical device according to claim 1, wherein the spacer member has the deployed radius to place the medical device at an angle of tilt with respect to a longitudinal axis of the vessel, and the angle of tilt is equal to or smaller than a maximum permitted angle of tilt.

4. The implantable medical device according to claim 1, wherein the spacer member has the deployed radius determined by the following equation:

$$R_{min} = (rad_d - b \tan x°),$$

where:
$R_{min}$ = minimum radius of the spacer member,
$rad_d$ = deployed maximum radius of the medical device,
b = the length of the leg elements measured in a longitudinal direction of the device from the second ends to the coupling member, and
x° = the maximum tilt angle of the filter.

5. The implantable medical device according to claim 4, wherein the spacer member has the deployed radius of no more than 150% of the minimum radius.

6. The implantable medical device according to claim 1, wherein the spacer member has a deployed diameter of no more than 50% of the maximum diameter of the medical device.

7. The implantable medical device according to claim 1, wherein each of the wire elements extends around a part of a circumference of the coupling member.

8. The implantable medical device according to claim 7, wherein the spacer member is formed of two or more curved wire elements disposed substantially radially opposite one another and which are circumferentially spaced from one another.

9. The implantable medical device according to claim 1, wherein each of the wire elements includes a curved vessel contact portion and a free end having a radius no greater than a radius of curvature of the vessel contact portion.

10. The implantable medical device according to claim 9, wherein each of the wire elements includes a reverse curved portion relative to the curvature of the vessel contact portion as the first portion.

11. The implantable medical device according to claim 10, wherein the reverse curved portion is adjacent the coupling member.

12. The implantable medical device according to claim 1, wherein each of the wire elements is attached at a first end to the coupling member and a second end is free.

13. The implantable medical device according to claim 1, wherein the spacer member lies at an angle of no more than ±25° from a plane normal to the longitudinal axis.

14. The implantable medical device according to claim 1, wherein the spacer member is made of flexible material.

15. The implantable medical device according to claim 1, wherein the spacer member is attached to the coupling member.

16. The implantable medical device according to claim 1, wherein the spacer member includes a circumferential perimeter.

17. The implantable medical device according to claim 1, wherein a circumferential perimeter of the spacer member has substantially the same radius around the coupling member.

18. The implantable medical device according to claim 1, wherein the coupling member includes a device retrieval element attached thereto.

19. A method of manufacture of an implantable medical device for a vessel, the medical device including a coupling member defining a longitudinal axis; a plurality of leg elements made of flexible material, each leg element including a first end connected to the coupling member and a second end remote from the connecting member, the leg elements extending in a deployed conical configuration from the coupling member to a maximum radius of the leg elements adjacent the second end of the leg elements, the second end of the leg elements defining a maximum diameter to the medical device; the method including the steps of:

forming a spacer member and disposing the spacer member proximate the coupling member, wherein the step of forming the spacer member includes sizing the spacer member to have a deployed radius less than the maximum radius of the leg elements, and forming the spacer member with a plurality of wire elements, and wherein each of wire elements includes a first portion and a second portion, and when viewed along the longitudinal axis from the second end, the first portion arcuately extends outward from the coupling member in a counterclockwise direction for a first length of the wire element and the second portion arcuately and continuously extends from the first portion in a clockwise direction for a second length of the wire element, which is greater than the first length, to a free end of the wire element, and the free end of each wire element is shaped to extend radially inward from a vessel contact portion of the wire element, or the first portion arcuately extends outward from the coupling member in the clockwise direction for a first length of the wire element and the second portion arcuately and continuously extends from the first portion in the counterclockwise direction for a second length of the wire element, which is greater than the first length, to a free end of the wire element, and the free end of each wire element is shaped to extend radially inward from a vessel contact portion of the wire element.

20. A method according to claim 19, wherein the step of forming the spacer member includes sizing the spacer member to have the deployed radius to place the medical device at an angle of tilt with respect to a longitudinal axis of the vessel, and the angle of tilt is equal to or smaller than a maximum allowed angle of tilt.

21. A method according to claim 19, wherein the step of forming the spacer member includes sizing the spacer member to have the deployed radius substantially determined by the following equation:

$$R_{min} = (\text{rad}_d - b \tan x°),$$

where:
$R_{min}$ = minimum radius of the spacer member,
$\text{rad}_d$ = deployed maximum radius of the medical device,
b = the length of the leg elements measured in a longitudinal direction of the device from the second ends to the coupling member, and
x° = the maximum tilt angle of the filter.

* * * * *